United States Patent [19]

DeFreitas et al.

[11] Patent Number: 5,427,781

[45] Date of Patent: Jun. 27, 1995

[54] METHOD OF ACTIVATING T CELLS WITH LYMPHOKINE SAF

[75] Inventors: Elaine DeFreitas, Villanova; J. Todd Abrams, Narberth, both of Pa.

[73] Assignee: University of Miami, Miami, Fla.

[21] Appl. No.: 84,996

[22] Filed: Jul. 2, 1993

Related U.S. Application Data

[60] Division of Ser. No. 628,621, Dec. 10, 1990, Pat. No. 5,225,535, which is a continuation-in-part of Ser. No. 284,558, Dec. 15, 1988, abandoned.

[51] Int. Cl.$^6$ .................... A61K 38/19; C07K 14/52
[52] U.S. Cl. .................... 424/851; 530/350; 530/351; 514/2; 514/8; 514/12; 424/545; 424/198.1; 435/240.2
[58] Field of Search ............... 530/351, 350; 424/85.1, 424/545, 198.1; 514/2, 8, 12; 435/240.2

[56] References Cited

U.S. PATENT DOCUMENTS 5,225,535  7/1993  DeFrietas et al. .................. 530/351

OTHER PUBLICATIONS

Balkwill and Burke *Immunol Today* 10(9):299-303 (1989).

Solbach et al., 1984, "Growth, Interleukin-2 Production, and Responsiveness to IL-2 in T4-Positive T Lymphocyte Population From Malignant Cutaneous T Cell Lymphoma (Sézary's Syndrome): The Effect of Cyclosporine A," *Blood*, 64(5):1022-1027.

Maeda et al., 1985, "Origin of Human T-Lymphotrophic Virus I-Positive T Cell Lines in Adult T Cell Leukemia," *J. Exp. Med.*, 162:2169-2174.

Okada et al., 1985, "TCGF (IL 2)-Receptor Inducing Factor(s), II. Possible role of ATL-derived factor (ADF) on constitutive IL 2 receptor expression of HTLV-I(+) T cell lines," *J. Immunol.* 135:3995-4003.

Yodoi et al., 1985, "TCGF (IL 2)-Receptor Inducing Factor(s), I. Regulation of II 2 Receptor on a Natural Killer-like Cell Line (YT Cells)," *J. Immunol.*, 134(3):1623-1630.

Rimsky et al., 1986, "Purification to Homogeneity and NH$_2$-terminal Amino Acid Sequence of a Novel Interleukin 1 Species Derived from a Human B Cell Line," *J. Immunol.*, 136:3304-3310.

Wakasurgi et al., 1987, "Epstein-Barr virus-containing B-cell line produces an interleukin 1 that it used as a growth factor," *Proc. Natl. Acad. Sci.* USA, 84:804-808.

Tagaya et al., 1988, "IL-2 Receptor(P55)/TAC-Inducing Factor, Purification and Characterization of Adult T Cell Leukemia-Derived Factor," *J. Immunol.*, 140:2614-2620.

Namen et al., 1988, "B Cell Precursor Growth-Promoting Activity, Purification and Characterization of a Growth Factor Active on Lymphocyte Precursors," *J. Exp. Med.*, 167:988-1002.

Maeda et al., 1988, "Application of a human T cell line derived from a Sézary syndrome patient for human interleukin 4 assay," *Immunol. Lett.*, 18(4):247-254.

Armitage et al., 1990, "Regulation of Human T Cell Proliferation by IL-7," *J. Immunol.*, 144:938-941.

Henney, 1989, "Interleukin 7: effects on early events in lymphopoiesis," *Immunol. Today*, 10:170-173.

*Primary Examiner*—Garnette D. Draper
*Assistant Examiner*—Shelly Guest Cermak
*Attorney, Agent, or Firm*—Banner, Birch, McKie & Beckett

[57] ABSTRACT

A lymphokine is taught which can be used to activate and stimulate CD3+, CD4+ T cells, as well as Sezary leukemic T cells. The lymphokine can be obtained from mitogen-stimulated peripheral blood mononuclear cells or urine of Sezary Syndrome patients. The lymphokine upregulates interleukin-2 receptors.

14 Claims, 11 Drawing Sheets

METHOD OF ACTIVATING T CELLS WITH LYMPHOKINE SAF

This application is a division of application Ser. No. 628,621, filed Dec. 10, 1990, now U.S. Pat. No. 5,225,535, which is a continuation-in-part of application Ser. No. 284,558, filed Dec. 15, 1988, now abandoned.

TECHNICAL FIELD OF THE INVENTION

The invention is in the field of lymphokines. More specifically it is in the field of T-cell stimulating factors.

BACKGROUND OF THE INVENTION

Lymphokines are protein or glycoprotein factors which are generally produced upon stimulation of T-cell cultures by mitogens or alloantigens. They display a variety of biological activities including: inhibiting DNA synthesis, inducing suppressor cells, inhibiting T-cell proliferation, inhibiting B cell immunoglobulin production, inhibiting B-cell growth. Because the lymphokines are often made by short-term cell cultures, it is often difficult to obtain sufficient material to do biochemical characterizations and compare various factors to each other.

The specificity of the lymphokines has raised great hopes for their use in human therapy. They can be used individually to stimulate underrepresented cell types or to inhibit growth of certain cells which may be proliferating in an uncontrolled manner. In combinations they may be able to modulate complex responses such as immune responses. Thus there is a continuing need and interest in the medical arts for new members of the lymphokine arsenal.

SUMMARY OF THE INVENTION

It is an object of the present invention to provide a new lymphokine.

It is another object of the invention to provide a lymphokine which can stimulate replication of helper T-cells.

It is yet another object of the invention to provide a lymphokine which can induce Tac protein (the interleukin 2 receptor).

It is still another object of the invention to provide a method of producing a lymphokine.

It is an object of the present invention to provide a method of treating Sezary Syndrome.

These and other objects of the invention are fulfilled by the following embodiments. In one embodiment a cell-free preparation of lymphokine SAF is provided which: stimulates replication of CD3+, CD4+ T cells; stimulates replication of long-term T cell lines in the presence of Il-2 but not in the absence of Il -2; induces Tac protein (Il-2 receptors) on Sezary T cells; has a molecular weight of 25 kD ±3 kD; and has an isoelectric point of about pH 5.0–6.5.

In another embodiment of the invention a method of producing a lymphokine preparation is provided, comprising: providing freshly isolated peripheral blood mononuclear cells from a Sezary Syndrome patient in a culture medium; treating the peripheral blood mononuclear cells with an effective amount of a T-cell mitogen to form a lymphokine; collecting the culture medium and removing the peripheral blood mononuclear cells from said medium to obtain the lymphokine preparation.

In yet another embodiment of the invention a method is provided of producing the lymphokine preparation, comprising: providing urine from a Sezary- Syndrome patient, said urine containing SAF activity; concentrating said SAF activity by adding ammonium sulfate to the urine to a final concentration of about 50% (w/v); collecting the precipitate formed in the urine and resuspending it in an appropriate physiological buffer; and, removing any excess ammonium sulfate from the resuspended precipitate to form the lymphokine preparation.

In still another embodiment of the invention a method of activating and stimulating CD3+, CD4+ T cells is provided comprising: providing CD3+, CD4+ T cells and treating said T cells with an effective amount of a lymphokine preparation containing SAF activity to increase Tac expression and stimulate proliferation of said CD3+, CD4+ T cells.

These and other embodiments will be apparent to those skilled in the art from the detailed disclosure which follows.

SAF can be used generally as an adjuvant of the immune system. For example, patients who are immunosuppressed by anti-cancer treatments, e.g., chemotherapy or radiotherapy, will benefit by stimulation with SAF. In addition patients having AIDS (autoimmune deficiency syndrome) or ARC (AIDS related complex) can have their helper T cell populations stimulated by SAF. SAF can also be useful in the treatment of genetic combined immunodeficiency syndrome (such as Wiscott-Aldrich syndrome) to stimulate T cell proliferation. Cocktails of SAF with other lymphokines may be desirable to stimulate a broad range of blood cells.

BRIEF DESCRIPTION OF THE DRAWINGS

FIG. 4A shows GM-CSF and Il-3; FIG. 4B shows Il-3 and Il-1.

FIG. 5A shows Il-3 and Il-4; FIG. 5B shows Il-5 and Il-6.

FIG. 6A shows Il-6 and Il -4; FIG. 6B shows Il-1 and Il-6.

FIG. 7A shows tumor necrosis factor-alpha; FIG. 7B shows lymphotoxin; FIG. 8A shows interleukin 6; and FIG. 8B shows GM-CSF.

DETAILED DESCRIPTION

A biological activity has been defined which has two distinct effects on a subclass of human lymphocytes. The activity (herein termed SAF) specifically affects helper T lymphocytes which are CD3+, CD4+. SAF activates target cells by increasing expression of receptors of the lymphokine interleukin-2 (Il-2). These receptors are also known as "Tac" protein or antigen. After about 48 hours in culture the Tac protein is maximally expressed. Interleukin-2 can then be bound by the activated cells; the binding stimulates DNA synthesis and cell proliferation.

SAF is known to stimulate Sezary T leukemic cells. Sezary Syndrome is ordinarily very difficult to treat with standard chemotherapeutic agents. This is due to the quiescent (non-dividing) state of most of the leukemia cells. Generally, chemotherapeutic agents achieve their selective effect (greater cytotoxicity to cancer cells than to normal cells) because cancer cells divide faster than normal cells and the chemotherapeutic agents act upon dividing cells. Therefore the use of SAF to stimulate proliferation of Sezary T cells would render these cells more susceptible to chemotherapeutic agents. SAF stimulates both resting T cells (peripheral blood mononuclear cells) and activated T cells (cell lines) from both Sezary Syndrome patients and healthy donors.

SAF has been characterized on the basis of its biochemical properties. The activity is sensitive to both pH variations and elevated temperature treatment. As can be seen in Table 9, partially purified SAF has an optimum pH at about 8.2. Although the activity is quite stable at 37° C., most of the activity is lost after a one-hour incubation at 56° C.

Figure 9A:
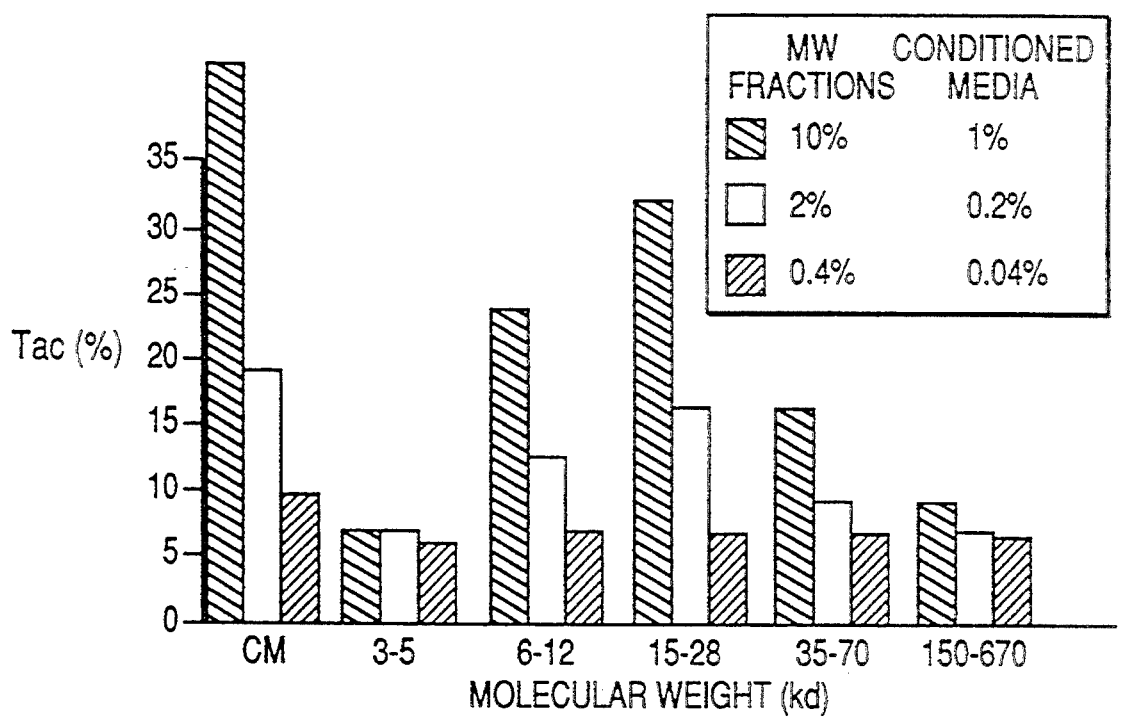
FIGS. 9A and 9B show the results of fractionation of SAF-containing conditioned media by gel filtration. The fractions were assayed for two activities: Tac-induction (FIG. 9A) and Sezary T cell proliferation (FIG. 9B). The two activities co-eluted.
Figure 9B:
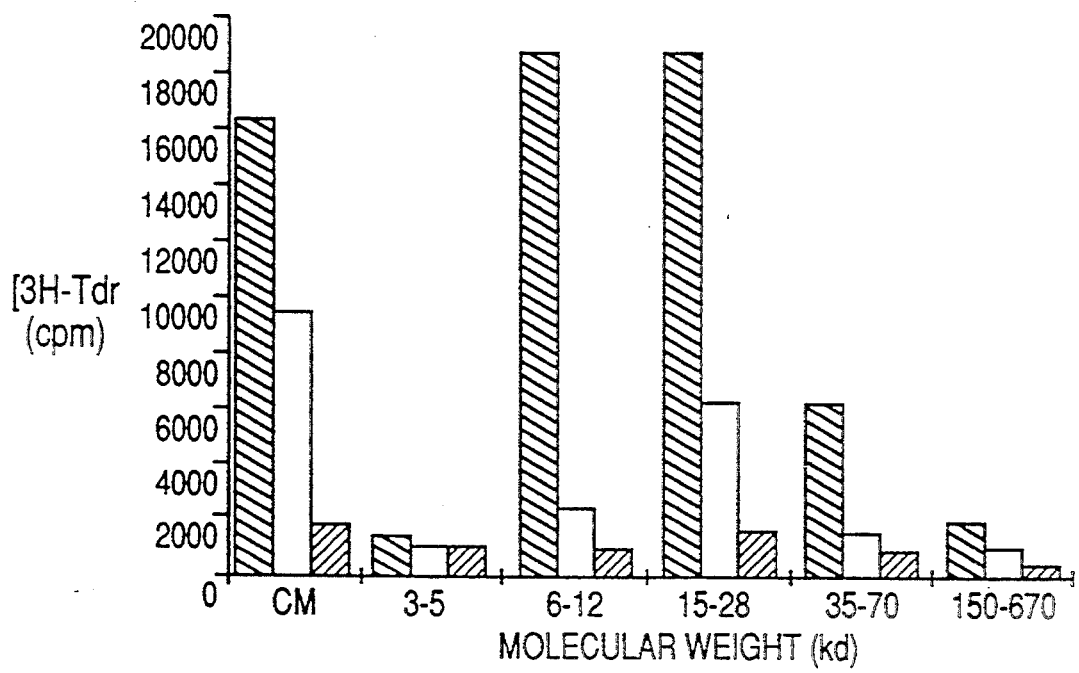

SAF activity does not bind to the carbohydrate moieties of Sephacryl ™, an agarose gel matrix. This clearly distinguishes it from Concanavalin A (the mitogen used to induce SAF production). The molecular weight range of SAF determined by gel filtration is between about 6 and 28 kD (see FIG. 9). The molecular weight of SAF as determined by gel electrophoresis in the presence of sodium dodecyl sulfate is in the range of 22 kD to 34 kD (see FIG. 11). The molecular weight of SAF is this about 22 kD to about 28 kD. When SAF activity is applied to an anion exchange column, it elutes in two peaks, at sodium chloride concentrations of 125 mM and 175 mM (see FIG. 10).

SAF can be found in a number of different biological source materials. For example, peripheral blood mononuclear cells (PBMC) produce SAF when treated with a T cell mitogen. Concanavalin A, as well as other known T cell mitogens, can be used to induce SAF production. Concentrations of concanavalin A above 0.1 mg/ml are generally mitogenic. PMBC from Sezary Syndrome patients most reliably produce SAF, although normal patients' PBMC have also been found to produce SAF. Another source of SAF is provided by the urine of Sezary Syndrome patients.

The culture medium of the mitogen-treated PBMC or urine can be treated to concentrate and/or purify the SAF activity. Any means known in the art of protein biochemistry can be used. Of course, care must be taken to preserve activity by keeping the activity in appropriate, non-denaturing conditions. As mentioned above, the activity is sensitive to both pH and temperature abuse.

One means among many of concentrating SAF activity from urine, for example, is to add ammonium sulfate to a final concentration of about 50%. As is known in the art, various proteins precipitate at certain ammonium sulfate concentrations, thus providing a ready means of concentration and purification from other components which remain in solution at the particular concentration. The precipitate can be resuspended in an appropriate buffer, such as phosphate buffered saline, pH 7.8, (PBS) and the remaining ammonium sulfate can be removed, for example, by dialysis against PBS.

Urine tends to be a dilute source of SAF. In contrast, conditioned media of mitogen-induced PBMC are highly concentrated. Conditioned media often must be diluted over one hundred-fold to achieve a linear response range.

As discussed above, any purification means known in the art can be employed. Applicants have successfully employed gel filtration and anion exchange chromatography. Once specific antibody is raised to SAF, immunoaffinity chromatography can be used to preparatively purify large amounts of SAF. Antibody can also be used to select cDNA clones which express SAF.

Two assays have been developed to detect and measure SAF activity. In one assay the induction of Tac protein (Il-2 receptors) on T-lymphocytes is measured. In the second assay proliferation of Sezary T cells is measured. Each of these assays is described below. Of course, other assays can be used to measure these same biological activities and such assays are also within the scope of the invention.

It is to be noted that the stimulation of proliferation of freshly isolated PBMC by SAF requires no added interleukin-2. However, stimulation of long-term Sezary T cell lines does require the addition of interleukin-2. This difference may be due to accessory cells present in the PBMC but not in T cell lines which produce interleukin-2 in situ. Alternatively, the cultured T cell lines may have lost the ability to synthesize interleukin-2 in culture.

Assays for determining levels of expression of Tac molecules may be performed according to any means known in the art. Generally, monoclonal antibodies specific for Tac are incubated with a sample containing T cells. The monoclonal antibody may be made according to Uchiyama, et al., J. Immunol., vol. 126, p. 1393 (1981). These are commercially available from the American Type Culture Collection, Rockville, Md., as well as from Becton Dickinson, Mountain View, Calif. The amount of antibody bound to the T cells may be measured, for example, by using a second antibody reactive with immunoglobulin molecules of the species of the first antibody. The second antibody can be conjugated to a fluor, such as FITC. The number of Tac-positive T cells can be determined by detection of fluorescence, for example, in a cytofluorograph. Alternatively, the anti-Tac antibodies can be labeled with the fluoresceinated isothiocyanate, in which case no second antibody is necessary for detection. Alternatively, the first antibody may be radiolabeled with $^{125}$I using, for example, the chloramine T method (see, McConahey, *Int. Arch. Allergy Appl. Immunol.*, vol. 29, p. 1885, 1986).

Interleukin 2 may be obtained from cultured medium or as a recombinant DNA product. The latter can be obtained for example from Ajinomoto Co. Ltd., Tokyo or Takeda Pharmaceutical Co. Ltd., Osaka, Japan. Cultured medium can be obtained by culture of human spleen cells in the presence of phytohemagglutinin and collecting the culture medium after growth.

Assays of T cell proliferation can be performed by any means known in the art. One such method can be carried out as follows. Freshly isolated peripheral blood mononuclear cells can be obtained by standard methods well known to those of skill in the art. Cells may be obtained from normal humans or from those displaying hematological disease. Approximately $2 \times 10^5$ cells can be distributed per microtiter well. Cells can be treated with reagents containing SAF for three days in a total volume of 200 $\mu$l. The cells can be pulsed with 1 $\mu$Ci/well tritiated deoxythymidine triphosphate ($^3$H-TdR) for the final 18 hours and harvested for liquid scintillation counting. In order to assay proliferation of a long-term Sezary T cell line instead of fresh PBMC, the cell treatment must also include interleukin-2 at about 50 U/ml.

Once SAF has been obtained, for example, from mitogen stimulated PBMC or urine as discussed above, it can be formulated in suitable buffers, carriers or media for the particular purpose desired. In most eases activity is essential, and therefore suitable preparations will stabilize activity rather than denature the protein. As discussed above, such preparations will preferably have a pH of about 8. If SAF is to be used to simulate cells in culture, then preparations compatible with cell growth will be desired. Such preparations may include other lymphokines, such as Il-2. For chemotherapeutic administration to Sezary Syndrome patients, preparations may contain cytotoxic drugs such as cytosine arabinoside or 5-fluoro-uridine. For stimulation of many different types of lymphocytes, SAF may be formulated and administered in a cocktail of lymphokines.

CD3$^+$, CD4$^+$ T cells can be identified using the T cell reagents available from Ortho Pharmaceutical Co., Raritan, N.J. These are also described in Kung U.S. Pat. Nos. 4,361,549; 4,361,550; 4,364,932-37. The CD3$^+$, CD4$^+$ T cells are a subset of T cells which express the CD3 and CD4 antigens.

Long-term Sezary T cell lines can be established according to the present invention by obtaining peripheral blood mononuclear cells from Sezary syndrome patients and culturing them in the presence of SAF and interleukin 2. Rapidly dividing T cells which grow out can be maintained in Il-2 with occasional restimulation with SAF. Periodic restimulation of derived T cell lines may be required using gamma-irradiated allogeneic PBMC with SAF and Il-2.

PBMC can be isolated as known in the art. Generally, heparinized peripheral blood is obtained from human donors, either normal donors or Sezary patients. The blood is diluted in a balanced salt solution such as Hanks', and layered over Ficoll-Hypaque, (available from Pharmacia Fine Chemicals, Piscataway, N.J.) and centrifuged at $350 \times g$ for 30 minutes at 18 °C. to obtain a mononuclear cell fraction.

The following working examples are not intended to limit the invention which is defined by the claims appended below.

EXAMPLE 1

This example demonstrates the response of freshly isolated PBMC to SAF-containing conditioned medium (SAF-CM).

Figure 1A:
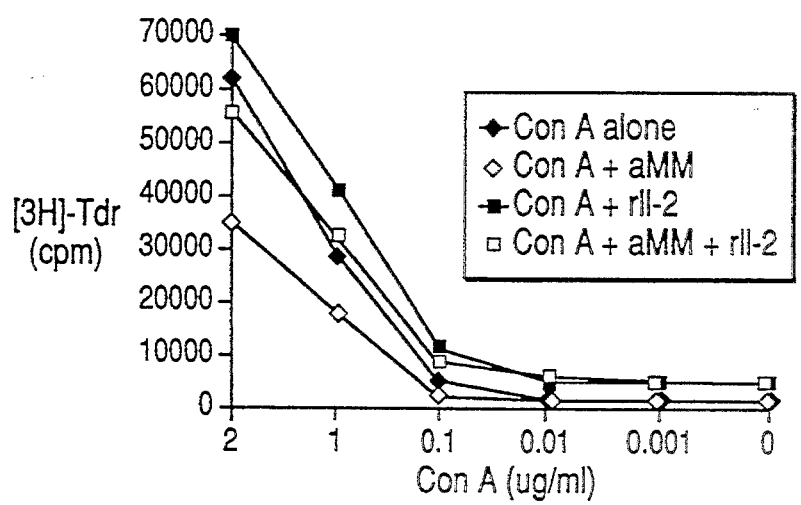
FIG. 1A depicts the response of freshly isolated peripheral blood mononuclear cells to concanavalin A (Con A).
Figure 1B:
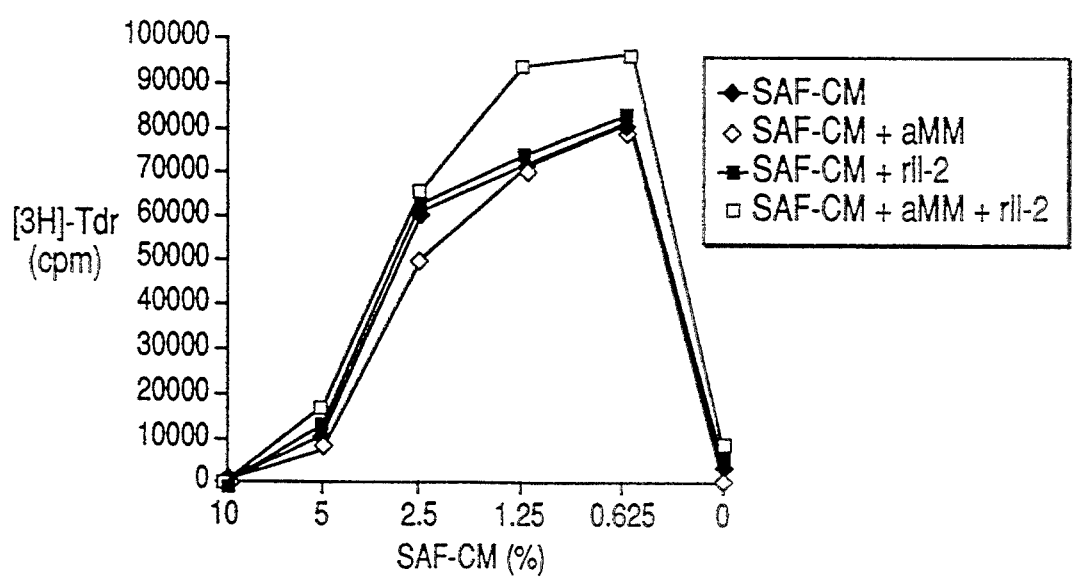
FIG. 1B depicts the response of freshly isolated peripheral blood mononuclear cells to SAF. The effects of alpha-methyl mannoside, interleukin-2 (IL-2), and both agents, with Con A and IL-2, are also depicted, respectively, in FIGS. 1A and FIG. 1B. The response measured was incorporation of deoxythymidine triphosphate.

PBMC ($2 \times 10^5$/well) were treated with various reagents (SAF-CM, alpha methyl mannoside (aMM) or interleukin-2 (Il-2), as indicated in FIG. 1B) for three days in a total volume of 200 $\mu$l. Plates were pulsed with 1 $\mu$Ci/well $^3$H-TdR for the final 18 hours and harvested for liquid scintillation counting. Data shown in FIG. 1B are the means of triplicates. S.E.M. was less than 10% of the means.

SAF-CM induced maximal proliferation at 0.625% final volume. The presence of exogenous r Il-2 had marginal effects on the overall response. It is noteworthy that the SAF-CM (at 100% concentration) used here and in other experiments contained 1 $\mu$g/ml Concanavalin A (Con A). Therefore, the maximal proliferative effects of SAF-CM containing con A were observed at con A concentrations of less than 10 ng/ml; such concentrations have been shown not to be mitogenic.

EXAMPLE 2

This example compares the effect of alpha methylmannoside on the activities of: (1) Concanavalin A and (2) SAF.

FIG. 1A shows a representative experiment wherein con A was titrated on PBMC in the presence and absence of 10 mg/ml alpha-methyl mannoside (aMM), a carbohydrate known to inhibit the mitogenic effects of con A. Con A was found to be mitogenic at concentrations above 0.1 mg/ml: aMM decreased this activity by about 50% at all concentrations tested. Con A concentrations below 0.1 mg/ml were not mitogenic even in the presence of saturating concentrations of r Il-2 (50 U/ml). As can be seen in FIG. 1B, aMM did not decrease the SAF activity at any concentration tested. Thus aMM affects SAF and con A activities differently.

Additional evidence supporting the hypothesis that con A is not SAF is: one, con A-containing "mock" CM (i.e., CM which was never exposed to cells) contained no SAF activity; two, con A binds to Sephacryl ™ and must be eluted with aMM. The majority of SAF activity elutes from a Sephacryl ™ S200 column with PBS pH 7.8. Third, SAF activity has been found in the urine of a highly leukemia Sezary Syndrome patient, where no con A was added or detected.

EXAMPLE 3

This example shows the requirements of interleukin-2 to achieve the proliferative response to SAF by long-term T cell lines.

Figure 2:
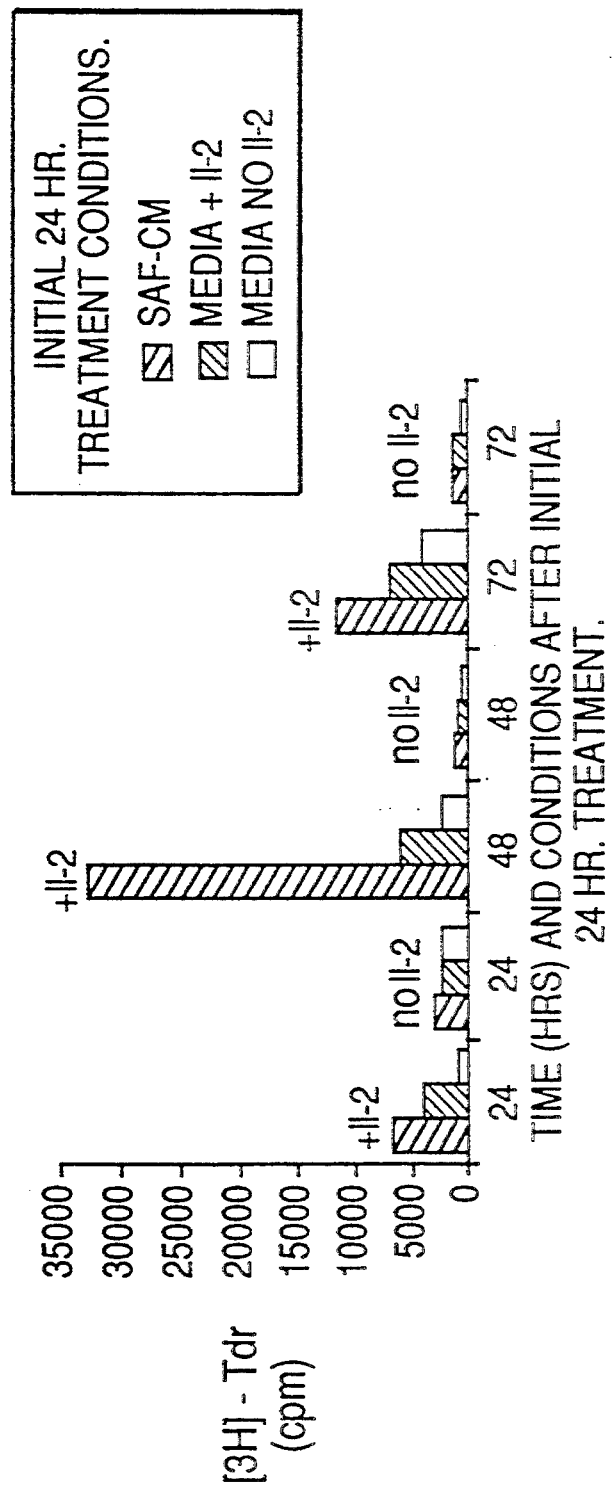
FIG. 2 shows the time course of response of a long-term Sezary T-cell line to SAF. Also shown is the need for interleukin 2 to obtain the full stimulatory effect of SAF.

A Sezary T cell line ($5 \times 10^4$/well) was treated with SAF-CM (0.6% final volume), media with r Il-2 (50 U/ml) or media without r Il-2 for 24 hrs. Thereafter, at 24 hr. intervals, r Il-2 (50 U/ml) was or was not added to each of the three initial groups. All groups (in triplicate) were pulsed with 1 $\mu$Ci/well $^3$H-TdR for the final 5 hrs. and harvested for liquid scintillation counting. Data shown in FIG. 2 are the mean of triplicates. S.E.M. was less than 10% of the mean.

After 24 hours of SAF stimulation, maximal proliferation is seen at 48 hours post r Il-2 addition. T-cells given only r Il-2 in the first 24 hrs. or later showed minimal levels of proliferation.

EXAMPLE 4

This example demonstrates that interleukin-2 cannot replace the function of SAF in stimulating proliferation of T-cell lines.

Figure 3A:
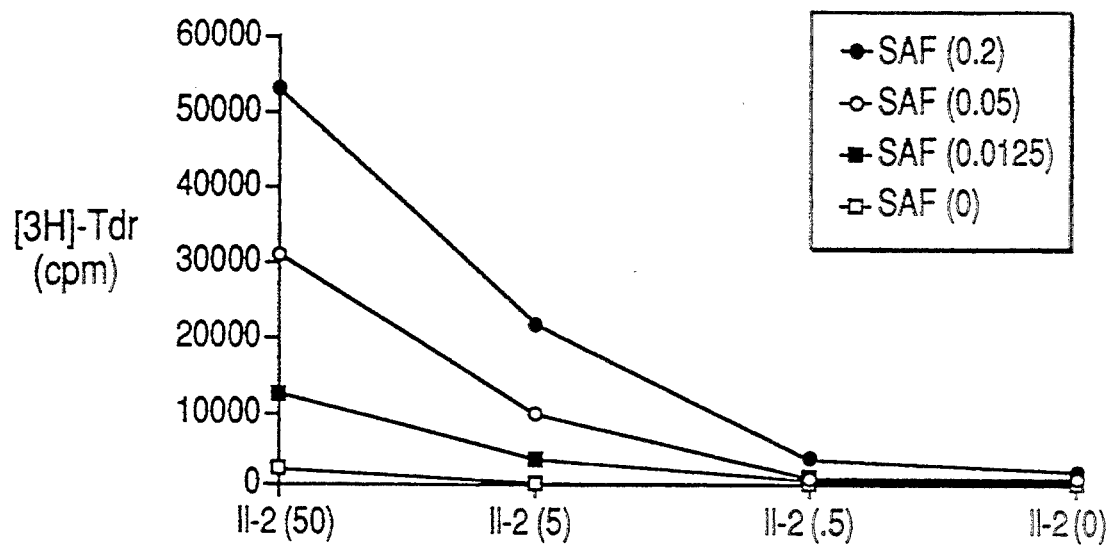
FIGS. 3A and 3B show that both interleukin 2 and SAF are required to obtain the proliferation of two Sezary T cell lines (FIGS. 3A and FIG. 3B, respectively) and that neither lymphokine can replace the role of the other.
Figure 3B:
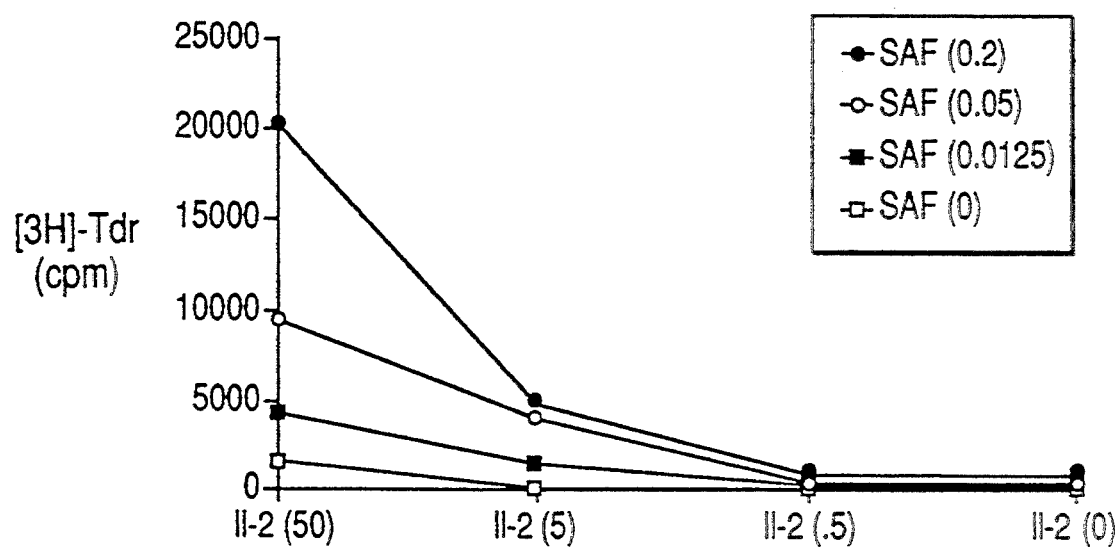
Figure 4A:
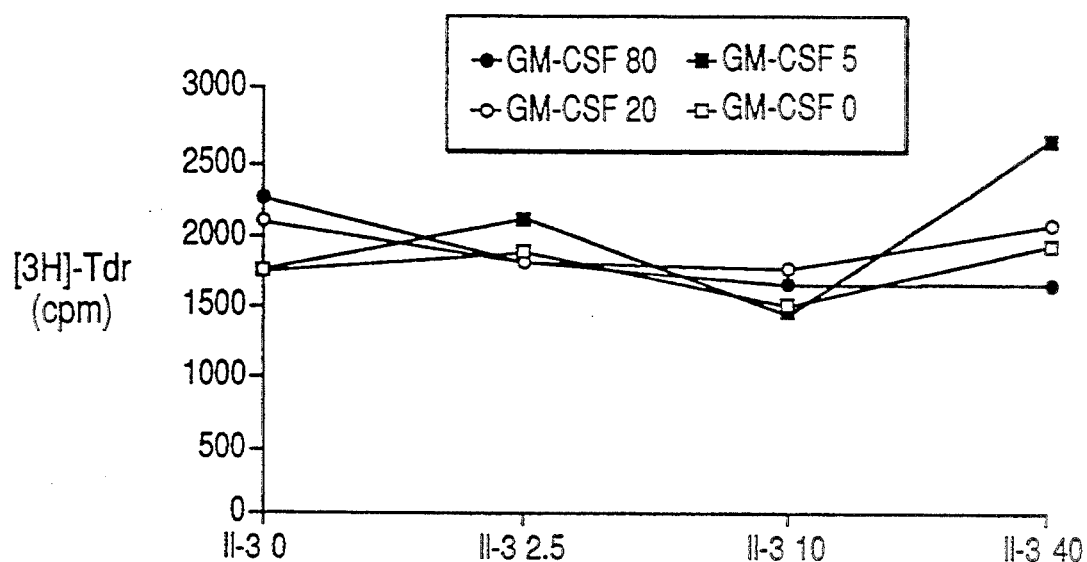
FIGS. 4A and 4B show the effect of combinations of lymphokines in the presence of interleukin-2 on the proliferation of a Sezary T cell line.
Figure 4B:
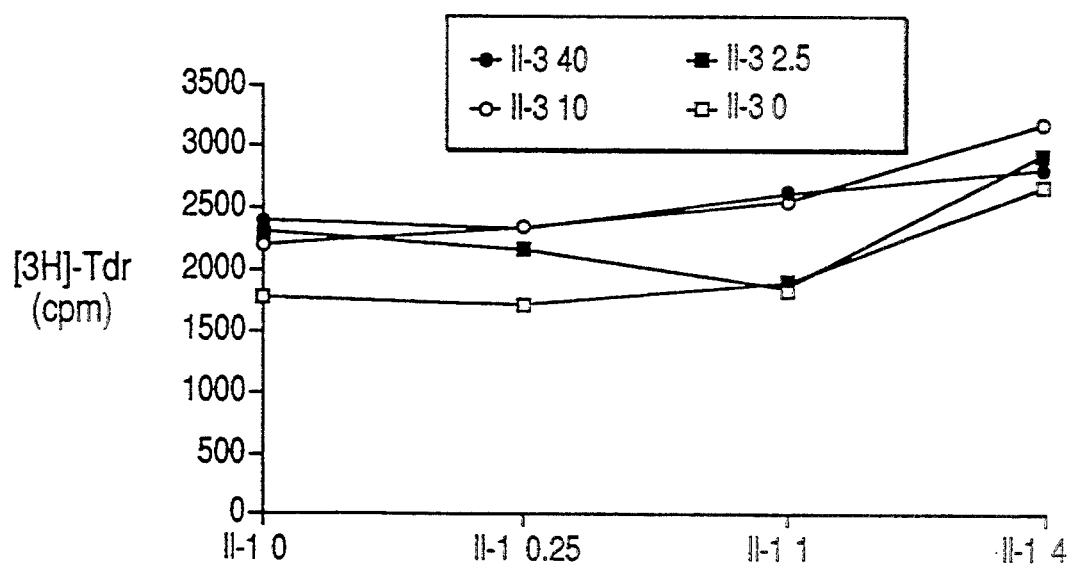
Figure 5A:
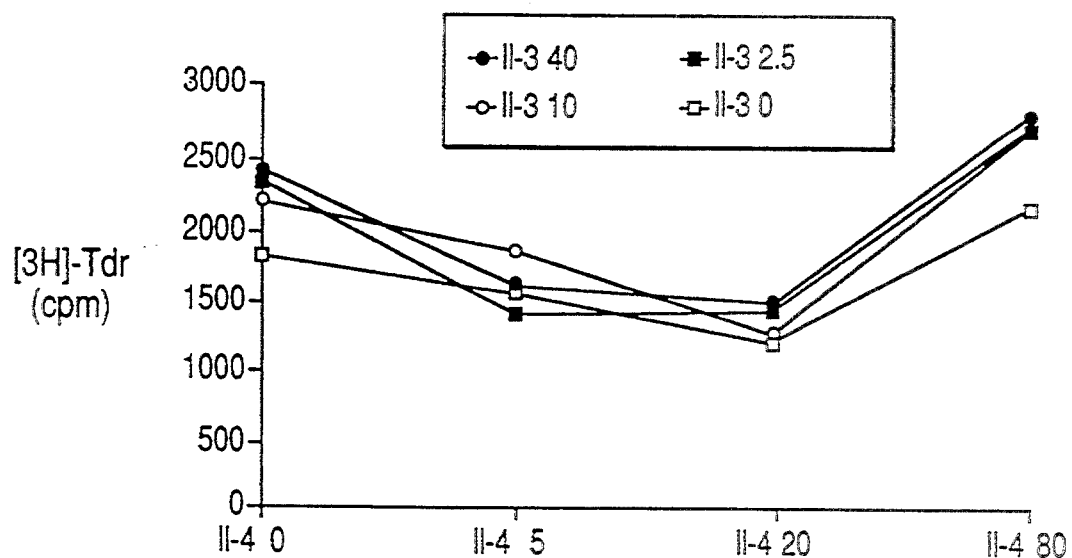
FIGS. 5A and 5B show the effect of combinations of lymphokines in the presence of interleukin 2 on the proliferation of a Sezary T cell line.
Figure 5B:
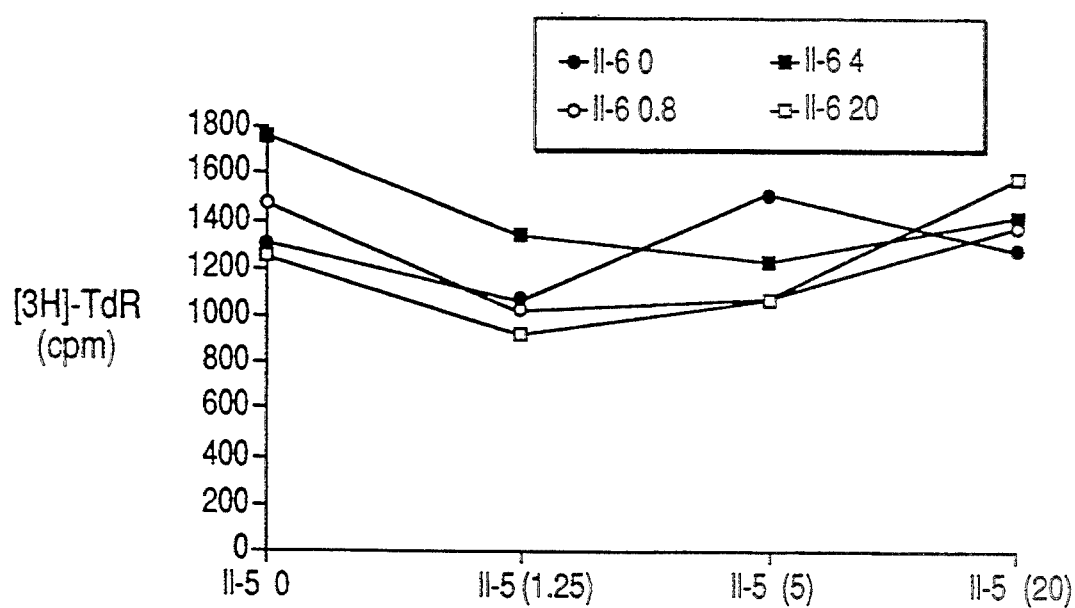
Figure 6A:
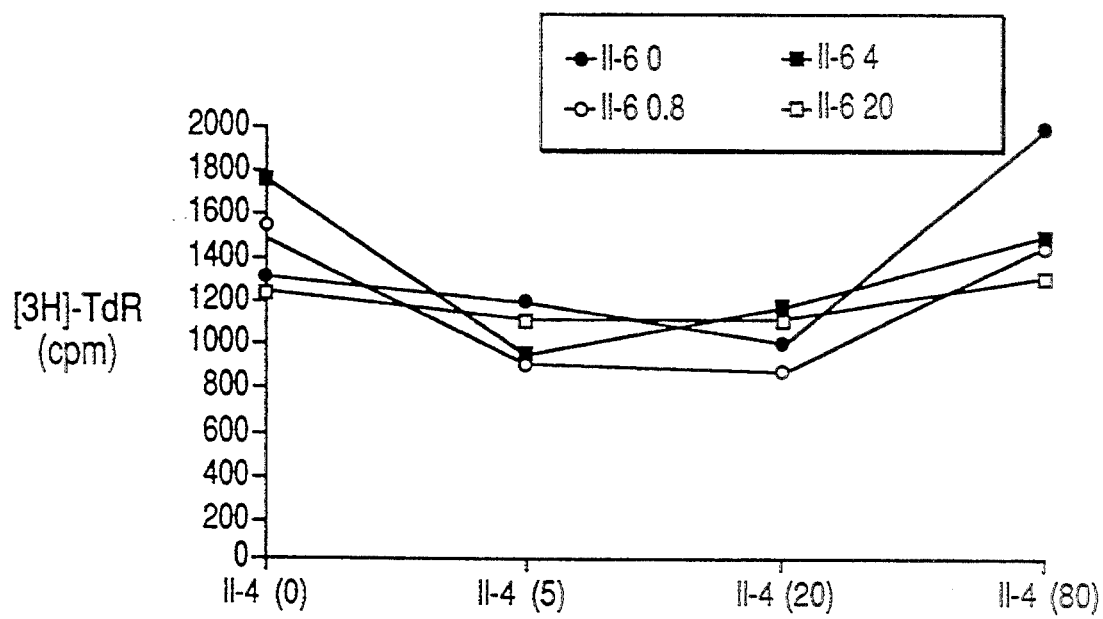
FIGS. 6A and 6B shows the effect of combinations of lymphokines in the presence of interleukin 2 on the proliferation of a Sezary T cell line.
Figure 6B:
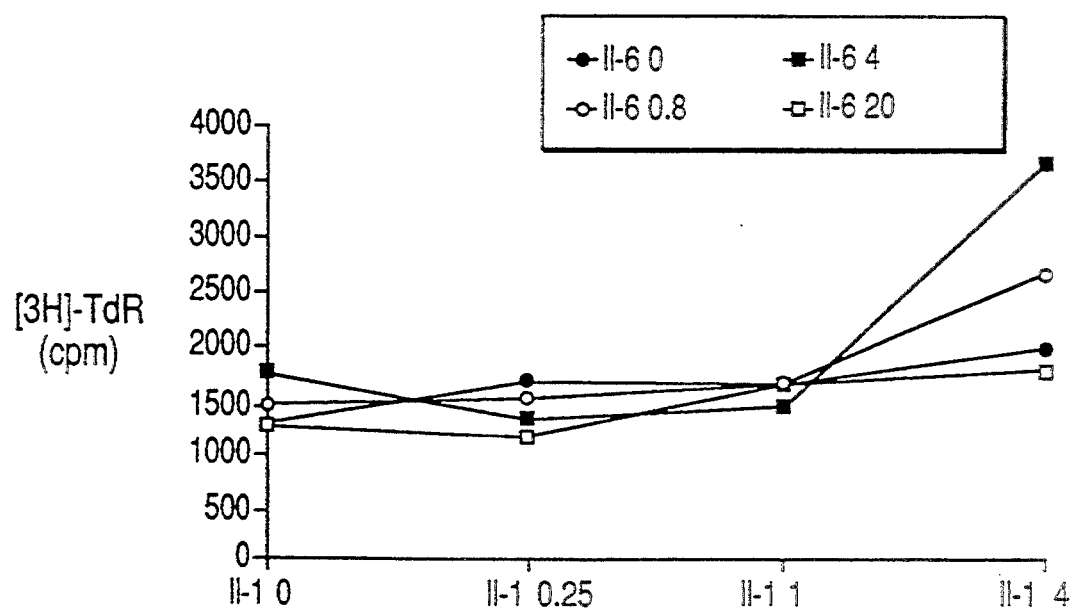

T cell lines from two Sezary Syndrome patients ($5 \times 10^4$/well) were treated with varying concentrations of r Il-2 and SAF-CM for three days. All groups were pulsed with 1 μCi/well $^3$H-TdR for the final 18 hrs., then harvested for liquid scintillation counting. Data shown in FIGS. 3A and 3B are the mean of triplicates. S.E.M. was less than 10% of the mean.

In the absence of SAF, no Il-2 concentration was capable of supporting the proliferation of these cell/lines. Similarly SAF alone stimulated no increase in $^3$H-TdR incorporation. At a single concentration of SAF, the proliferation measured was dependent on the concentration of r Il-2 present. These data and those found in FIG. 2 clearly demonstrate that the Tac-inducing function of SAF cannot be replaced with r Il-2 and that the increase in DNA synthesis as a measure of cell/replication requires both SAF and r Il-2. Moreover, CM containing high levels of SAF activity were routinely tested for Il-2 in an Il-2 bioassay and were always found to be negative.

EXAMPLE 5

This example demonstrates that ten known cytokines do not have SAF activity.

Table 1 illustrates one of three experiments designed to evaluate Il-1 in an SAF assay. At concentrations from 10 U/ml to 0.1 U/ml, wherein 1 U/ml yielded half-maximal activity in Il-1 comitogenesis assays, Il-1 showed no Tac-inducing activity nor proliferative effect on Sezary T cell lines in the presence of 50 U/ml r Il-2. Table 1 also shows a representative experiment which demonstrates that interferon-gamma (at bioactive concentrations in interferon assays) does not induce Tac protein on T cells nor does it cause T cell proliferation in the presence of r Il-2.

TABLE 1

SAF ACTIVITY IS NOT MEDIATED BY Il-1 OR BY IFN-GAMA

| Factor Added[a] | Tac Expression (%) | Proliferation ($^3$H-TdR, cpm)[c] |
|---|---|---|
| rIl-2 only | 1.5 | 2,064 |
| SAF-CM[b] | 24.1 | 29,373 |
| r-IFN-gamma | | |
| 100 U/ml | 8.1 | 2,172 |
| 10 U/ml | 9.2 | 1,649 |
| 1 U/ml | 5.3 | 1,237 |
| media | 8.9 | 4,008 |
| SAF-CM | 43.7 | 35,724 |
| Il-1: | | |
| 10 U/ml | 13.3 | 2,062 |
| 1 U/ml | 13.3 | 4,625 |
| 0.1 U/ml | 12.4 | 3,580 |

[a]rIl-2 used at 50 U/ml final concentration.
[b]SAF-CM used at 1% final volume.
[c]Data is the mean of triplicates; S.E.M. was less than 10% of the mean.

Il-3, a 26 kD growth factor for a variety of myeloid cells and their progenitors (formerly called multi-CSF), has recently been shown to induce Tac protein on hematopoietic stem cells, although these receptors were all of low affinity and non-functional. GM-CSF (molecular weight 25–30 kD), which stimulates growth of granulocyte and macrophage progenitors, has recently been reported to support the proliferation and long term growth of some Il-2-dependent T cell clones. For these reasons, we tested both human Il -3 and GM-CSF for SAF activity by titrating them over their bioactive concentration range on Sezary T cells in the presence of r Il-2. The results are shown in Table 2. None of these hematopoietic colony stimulating growth factors showed any effect on the T cell lines.

TABLE 2

NEITHER INTERLEUKIN 3 NOR GM-CSF HAVE SAF ACTIVITY

| Factor added[a] | | $^3$H-TdR (cpm) |
|---|---|---|
| r Il-2 only | | 957 |
| SAF: | 0.20% | 21,396 |
| | 0.05% | 10,394 |
| | 0.01% | 3,789 |
| Il-3: | 40 U/ml | 1,602 |
| | 10 U/ml | 1,670 |
| | 2.5 U/ml | 1,271 |
| GM-CSF | 80 U/ml | 1,147 |
| | 20 U/ml | 1,112 |
| | 5 U/ml | 1,156 |

[a]r Il-2 was added at 50 U/ml final concentration.

A group of lymphokines involved in B cell activation and differentiation have recently been purified and their genes cloned. Il-4, a 20 kD protein formerly called B cell stimulatory factor I (BSF I), has been shown to be a growth factor for murine T cells, mast cells, and myelomonocytic cell lines. Il-5, a 50 kD protein formerly called T cell replacing factor or eosinophilic differentiation factor, was shown to induce cytotoxic T cells in the presence of Il-2. Il-6, a 26 kD protein (formerly called BSF 2) which induces terminal differentiation of B cells into plasma cells, was also shown to upregulate Tac on Tac-negative human T cell leukemia cells. For these reasons, we tested Il-4, Il-5, and Il-6 for SAF activity as previously described. The results of one such experiment are shown in Table 3. No single recombinant cytokine was capable of producing the SAF activity found in our conditioned media.

TABLE 3

INTERLEUKINS 4, 5 AND 6 DO NOT DEMONSTRATE SAF ACTIVITY

| Factor added[a] | | $^3$H-TdR (cpm) |
|---|---|---|
| r Il-2 only | | 1,309 |
| SAF: | 0.20% | 20,968 |
| | 0.05% | 11,551 |
| | 0.01% | 6,924 |
| Il-4: | 80 U/ml | 1,980 |
| | 20 U/ml | 992 |
| | 5 U/ml | 1,159 |
| Il-5: | 20 U/ml | 1,251 |
| | 5 U/ml | 1,503 |
| | 1.25 U/ml | 1,035 |
| Il-6: | 20 U/ml | 2,235 |
| | 4 U/ml | 3,146 |
| | 0.8 U/ml | 1,876 |

[a]Il-2 was added at 50 U/ml final concentration.

Tumor necrosis factor alpha (TNF), and beta (also known as lymphotoxin, LT), and epidermal growth factor (EGF) were also examined for SAF activity. Table 4 shows that none of these cytokines individually have SAF activity even when tested in the presence of saturating concentrations of Il-2.

TABLE 4

NEITHER TNF ALPHA, TNF BETA (LYMPHOTOXIN), NOR EGF CAN SUBSTITUTE FOR SAF

| Factor added[a] | | $^3$H-TdR (cpm) |
|---|---|---|
| R Il-2 only | | 1,733 |
| SAF: | 0.20% | 37,304 |
| | 0.05% | 19,729 |
| | 0.01% | 7,397 |
| TNF-alpha: | 80 U/ml | 2,115 |
| | 20 U/ml | 2,112 |
| | 5 U/ml | 2,187 |
| TNF-beta | 100 U/ml | 2,247 |
| (lymphotoxin) | 20 U/ml | 2,225 |
| | 4 U/ml | 1,878 |
| EGF: | 50 U/ml | 1,353 |
| | 5 U/ml | 1,373 |
| | 0.5 U/ml | 1,479 |

[a]r Il-2 was added at 50 U/ml final concentration.

EXAMPLE 6

This example shows that combinations of known cytokines do not have SAF proliferative activity.

Because synergistic activities of two cytokines on target cells have been reported, (e.g., gamma interferon upregulates cellular receptors for TNF alpha), we tested combinations of two of the above known cytokines for SAF activity. FIGS. 4A, 4B, 5A, 5B, 6A and 6B show representative experiments wherein two Cytokines were titrated against each other on an SAF-responsive Sezary T cell/line. An experiments shown were performed in the presence of r Il-2 (50 U/ml).

r GM-CSF and r Il-3 (FIG. 4A) and Il-1 and Il-3 (FIG. 4B) were titrated against each other in the presence of r Il-2 (50 U/ml) on 5×10$^4$ cells/well of a Sezary T cell Line in triplicate and incubated for 3 days. Plates were pulsed for the final 18 hrs. with $^3$H-TdR as previously described. Numbers in parentheses on the figure are the units per ml of each cytokine in its respective bioassay. The SAF-positive control was 50,861 cpm at 0.2% SAF-CM with r Il-2. r Il-2 alone gave 2144 cpm. Data are the mean of triplicates. S.E.M. was less than 10% of the mean. As can be seen, SAF activity cannot be replaced by combinations of Il-3 with GM-CSF or Il-1.

r Il-3 and r Il-4 (FIG. 5, panel A) and r Il-5 and Il-6 (FIG. 5B) were titrated against each other. The SAF-positive control yielded 20,968 cpm at 0.2% SAF-CM with r Il-2. r Il-2 alone gave 1950 cpm. Data are the mean of triplicates. S.E.M. was less than 10% of the mean. As can be observed readily, combinations of Il-3 and Il-4 or Il-5 and Il-6 cannot mimic SAF activity.

r Il-6 and r Il-4 (FIG. 6A) and Il-1 and Il-6 (FIG. 6B) were titrated against each other. The SAF-positive control gave 37,304 cpm at 0.2% SAF-CM with r Il-2 (50 U/ml). r Il-2 alone gave 1763 cpm. Data are the mean of triplicates. S.E.M.-was less than 10% of the mean. Combinations of Il-6 with either Il-1 or Il-4 do not mimic SAF activity.

Although some combination of two cytokines slightly (1–2 fold) augmented the proliferative response to Il-2, no combination of known lymphokines was found to mimic the magnitude of the SAF activity found in the SAF-CM.

Table 5 is a summary table showing the results of experiments performed in which cytokines were tested singly, in pairs of two, and with titrations of SAF. The combinations of two known cytokines tested to date are all combinations reported to synergize in at least one biologic assay. As seen, no combination induced proliferation except SAF and r Il-2.

TABLE 5

CYTOKINE COMBINATIONS TESTED FOR SAF ACTIVITY[a]

| | \multicolumn{11}{c}{T cell Response to b} |
|---|---|---|---|---|---|---|---|---|---|---|---|

| | Il-1 | Il-2 | Il-3 | Il-4 | Il-5 | Il-6 | GM-CSF | TNF alpha | TNF beta | EGF | IFN-Y |
|---|---|---|---|---|---|---|---|---|---|---|---|
| SAF | (−) | (+) | (−) | (−) | (−) | (−) | (−) | (−) | (−) | (−) | (−) |
| Il-1 | (−) | | | | | | | | | | |
| Il-2 | (−) | (−) | | | | | | | | | |
| Il-3 | (−) | (−) | (−) | | | | | | | | |
| Il-4 | (−) | (−) | (−) | (−) | | | | | | | |
| Il-5 | ND[c] | (−) | ND | ND | (−) | | | | | | |
| Il-6 | (−) | (−) | (−) | (−) | (−) | (−) | | | | | |
| GM-CSF | (−) | (−) | (−) | ND | (−) | (−) | (−) | | | | |
| TNF alpha | ND | (−) | (−) | (−) | (−) | (−) | ND | (−) | | | |
| TNF beta | (−) | (−) | (−) | ND | ND | (−) | (−) | ND | (−) | | |
| EGF | (−) | (−) | ND | ND | (−) | (−) | ND | (−) | (−) | (−) | |
| IFN-y | ND | (−) | ND | ND | ND | ND | ND | ND | ND | ND | (−) |

[a]All combinations were tested in the presence of 50 U/ml r Il-2 on a long-term T cell line from a Sezary patient. Titrations of each cytokine were performed in all assays.
[b]Negative (−) sign means less than two-fold proliferation above that seen with r Il-2 alone, or SAF alone in experiments using combinations of know cytokines with SAF. Positive (+) sign means proliferation at least ten-fold above r Il-2 alone.
[c]ND = not yet done.

EXAMPLE 7

This example shows that other cytokines do not augment the activity of SAF.

Figure 7A:
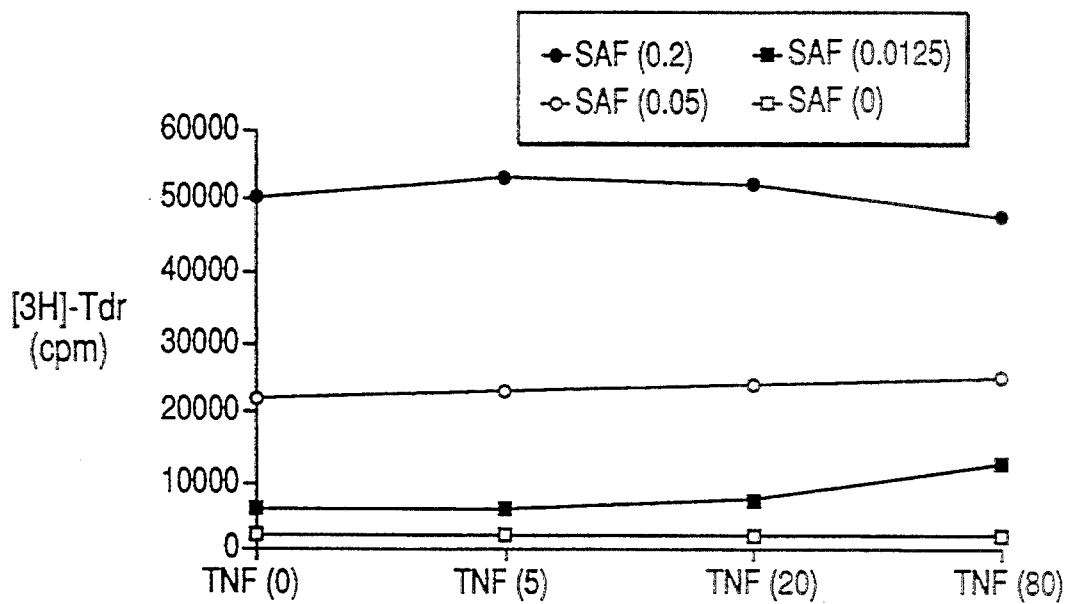
FIGS. 7A, 7B, 8A and 8B show the effect of additional lymphokines on the proliferation of a Sezary T cell line in the presence of SAF and Il-2.
Figure 7B:
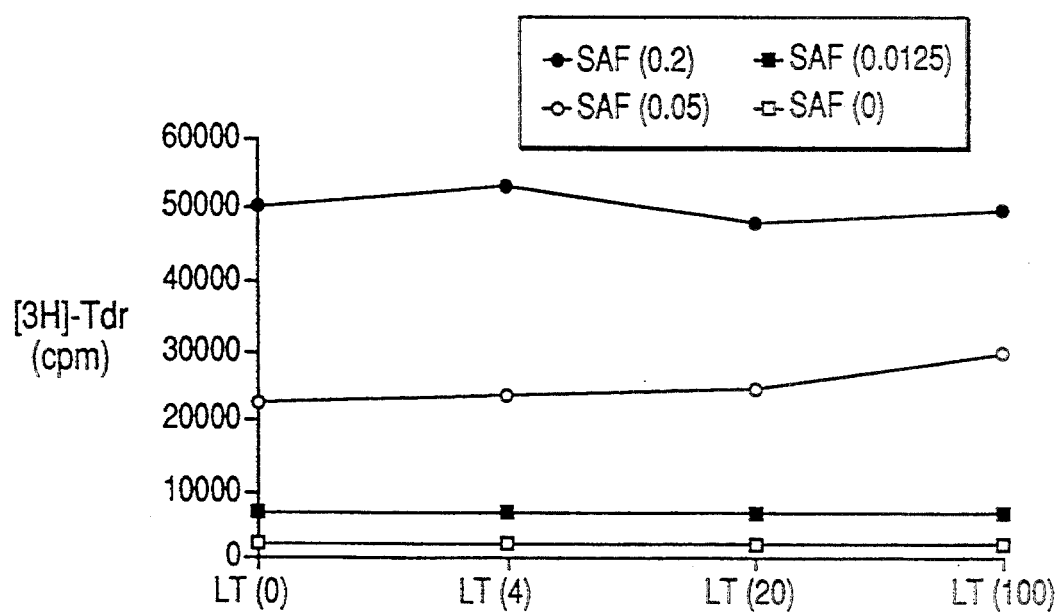
Figure 8A:
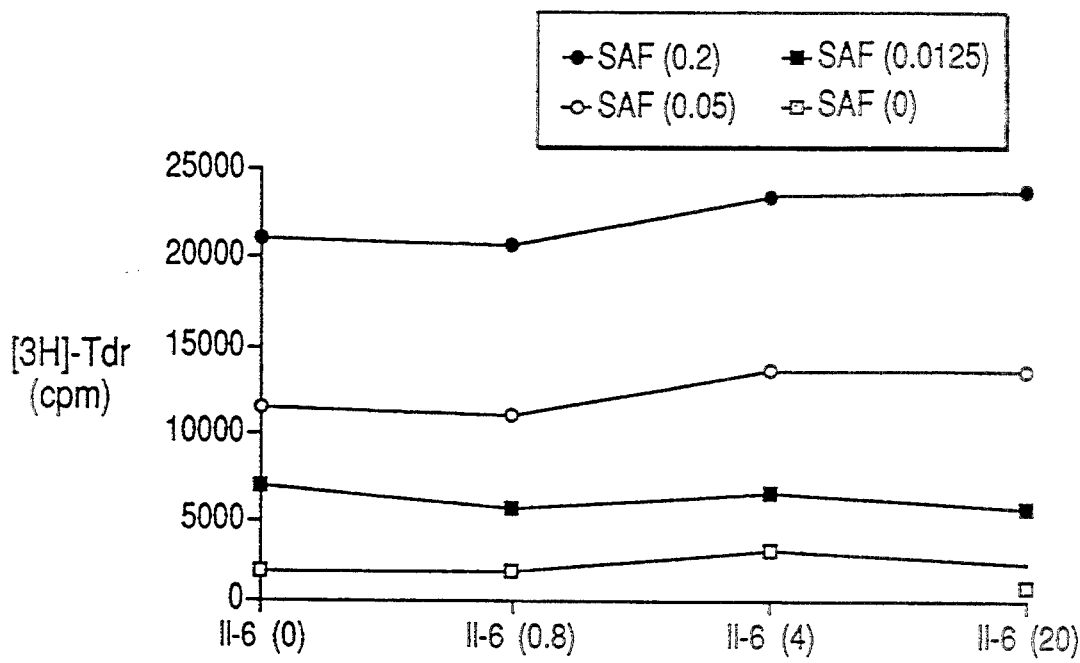
Figure 8B:
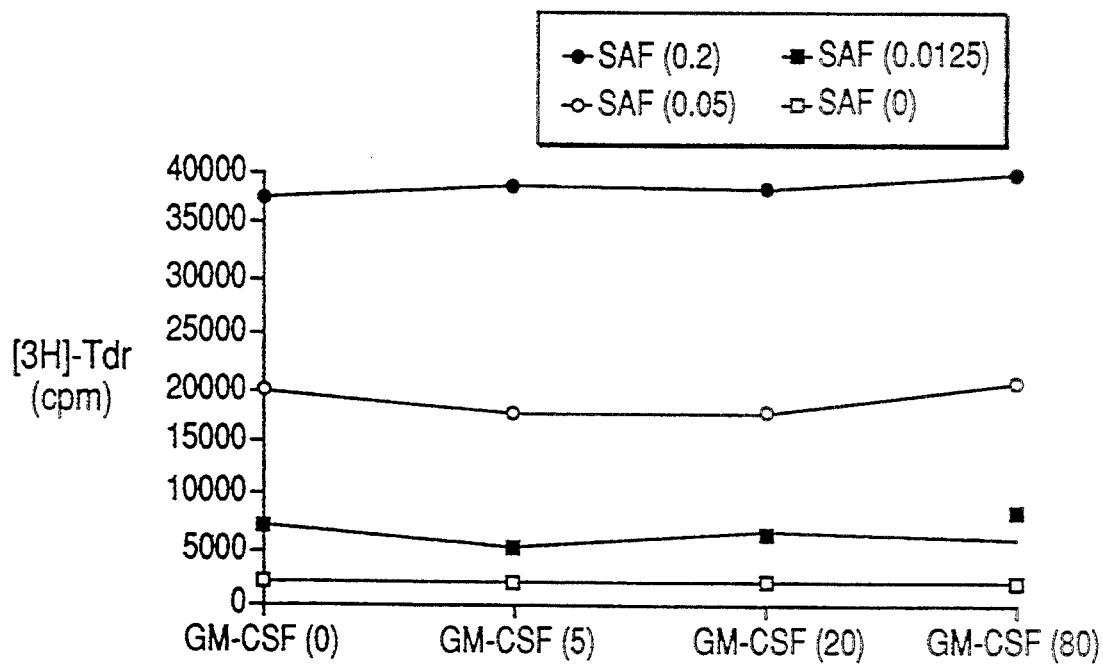

To determine if SAF is a combination of more than two known cytokines, dilutions of each known cytokine were tested in the presence of varying concentrations of SAF. If SAF activity is due to more than two known lymphokines, it was reasoned that addition of one of these factors would augment SAF potency at limiting SAF dilutions.

r TNF-alpha (FIG. 7A) and r LT (FIG. 7B) were added in varying amounts to a titration of SAF on long term Sezary T cell line in the presence of 50 U/ml r Il-2. r Il-2 alone gave 2144 cpm. Data are the mean of triplicates. S.E.M. was less than 10% of the mean.

r Il-6 (FIG. 8A) and r GM-CSF (FIG. 8B) were added in varying amounts to a titration of SAF on a long term Sezary T cell line with r Il-2 (50 U/ml) as described in FIG. 4. r Il-2 alone gave 1763 cpm. Data are the mean of triplicates. S.E.M. was less than 10% of the mean.

FIGS. 7A, 7B, 8A and 8B show representative experiments wherein no known cytokine provided an additive effect to any SAF dilution.

The following Table lists the cytokines tested for SAF activity and their sources. None were found with SAF activity.

TABLE 6

KNOWN CYTOKINES TESTED FOR SAF ACTIVITY

| Cytokines Tested | Assay used for Bioactivity | Source of Cytokine |
|---|---|---|
| Il-1 (Natural: alpha and beta) | Thymocyte comitogenesis assay | Genzyme |
| Il-2 (rec) | CTLL bioassay | Amgen |
| Il-3 (rec) | Colony-forming assay | Genzyme |
| Il-4 (rec) | PHA comitogenesis assay | Genzyme |
| Il-5 (rec) | B cell growth and differentiation | Genetics Institute |
| Il-6 (rec) | Thymocyte comitogenesis assay and marrow colony-forming assay | G. Trinchieri and Genetics Institute |
| TNF-alpha (rec) | Fibroblast cytotoxicity | G. Trinchieri |
| TNF-beta (rec) (a.k.a. Lymphotoxin) | NK activation | G. Trinchieri |
| GM-CSF (rec) | Proliferation of GM-CSF-dependent clone | G. Rovera and Genetics Institute |
| IFN-gamma (natural and rec) | Induction of HLA class II antigens | Amgen |
| EGF | Growth of fibroblasts; Melanoma growth assay | M. Herlyn and Collaborative Research Lab. |

EXAMPLE 8

This example shows a partial purification of SAF activity and some characterization of the partially purified material.

SAF was induced from PBMC of a highly leukemic Sezary Syndrome patient by stimulating $5 \times 10^6$ cells/ml with 1 μg/ml Con A for 48 hours. Supernatant (50 ml) was precipitated with 50% ammonium sulphate, dialyzed against PBS pH 7.8, concentrated, and applied to a precalibrated Sephacryl TM S200 column.

One ml fractions were collected and pools of three fractions were tested for Tac-inducing activity (in the absence of r Il-2) (FIG. 9A) and proliferative activity (with 50 U/ml r Il-2) (FIG. 9B) on a long term Sezary T cell line. Activity in each pool is compared with activity in the original SAF-CM (shown on the left). As shown, Tat-inducing activity and proliferative activity co-eluted at a molecular weight range between 6 and 28 kD and was dose-dependent on the dilution of SAF used. Seventy percent of the total SAF units applied to the S200 column eluted from the column using PBS, showing that SAF does not bind to the carbohydrates found on Sephacryl TM.

Figure 10:
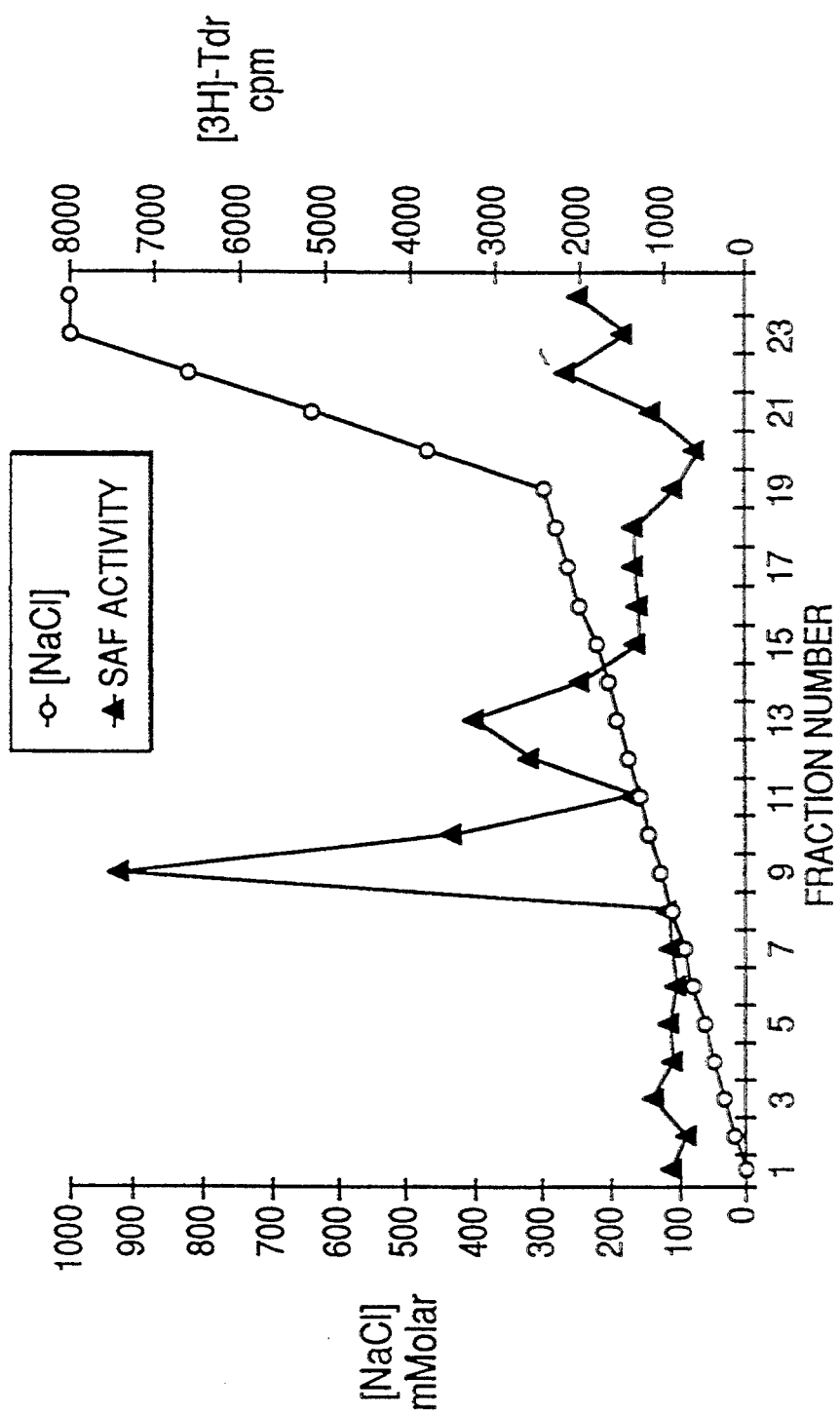
FIG. 10 depicts the elution profile of the 6–28kD fractions from gel filtration after fractionation on an anion exchange column. Two peaks of SAF activity were found.

A fraction pool of molecular weight 6–28 kD was applied to an anion exchange column (DEAE-Sephadex TM), eluted with a linear gradient of NaCl, and fractions dialyzed and tested individually for SAF activity (cell proliferation assay) as previously described (FIG. 10). Two peaks of activity were found; the major peak was seen at 125 mM NaCl and a minor peak seen at 175 mM NaCl. Preliminary data on the isoelectric focusing point of the two peaks of activity are consistant with their NaCl elution profile, i.e., the protein is relatively acidic (pI between pH 5.0–6.5).

The bioactivity of partially purified SAF was tested for stability at elevated temperatures and over a range of acidities. Stimulation of incorporation of tritiated deoxythymidine was measured. The activity was sensitive to prolonged (24 hrs.) pH exposure at pH 8.2 and heat treatment of 56° C. for 60 min (Table 7).

TABLE 7

SAF ACTIVITY IS pH- AND HEAT-LABILE

| Treatment[a] | Activity (% of control)[b] |
|---|---|
| pH | |
| 2.2 | 5 |
| 4.0 | 9 |
| 6.0 | 19 |
| 7.0 | 35 |
| 8.2 | 96 |
| 10.5 | 25 |
| Heat | |
| 27° C., 60 min. | 100 |
| 56° C., 60 min. | 33 |
| 70° C., 60 min. | 3 |
| 70° C., 30 min. | 3 |
| 70° C., 15 min. | 5 |

[a]SAF activity was determined using partially-purified material (SAF-pp).
[b]Assay used for SAF activity was Il-2 dependent proliferation of a T cell line. SAF-pp untreated and r Il-2 treatment induced 57% Tac-positive cells and 18,861 cpm ³H-TdR incorporation.

EXAMPLE 9

This example shows the molecular weight of SAF as determined by polyacrylamide gel electrophoresis in the presence of sodium dodecyl sulfate.

Five hundred units of SAF in beta-mercaptoethanol was electrophoresed on an SDS-polyacrylamide gel, and then the gel was cut into slices. Protein was eluted from each slice, and the SDS was removed by dialysis against a biological buffer solution. Eluted material was then tested at a 1:20 dilution for its ability to induce T cell proliferation, as measured by ³H-thymidine incorporation in the presence of 5 U/ml recombinant Il-2. The molecular weight of the proteins eluting in each slice was determined by comparison to the migration of molecular weight standards run simultaneously in the same gel.

Figure 11:
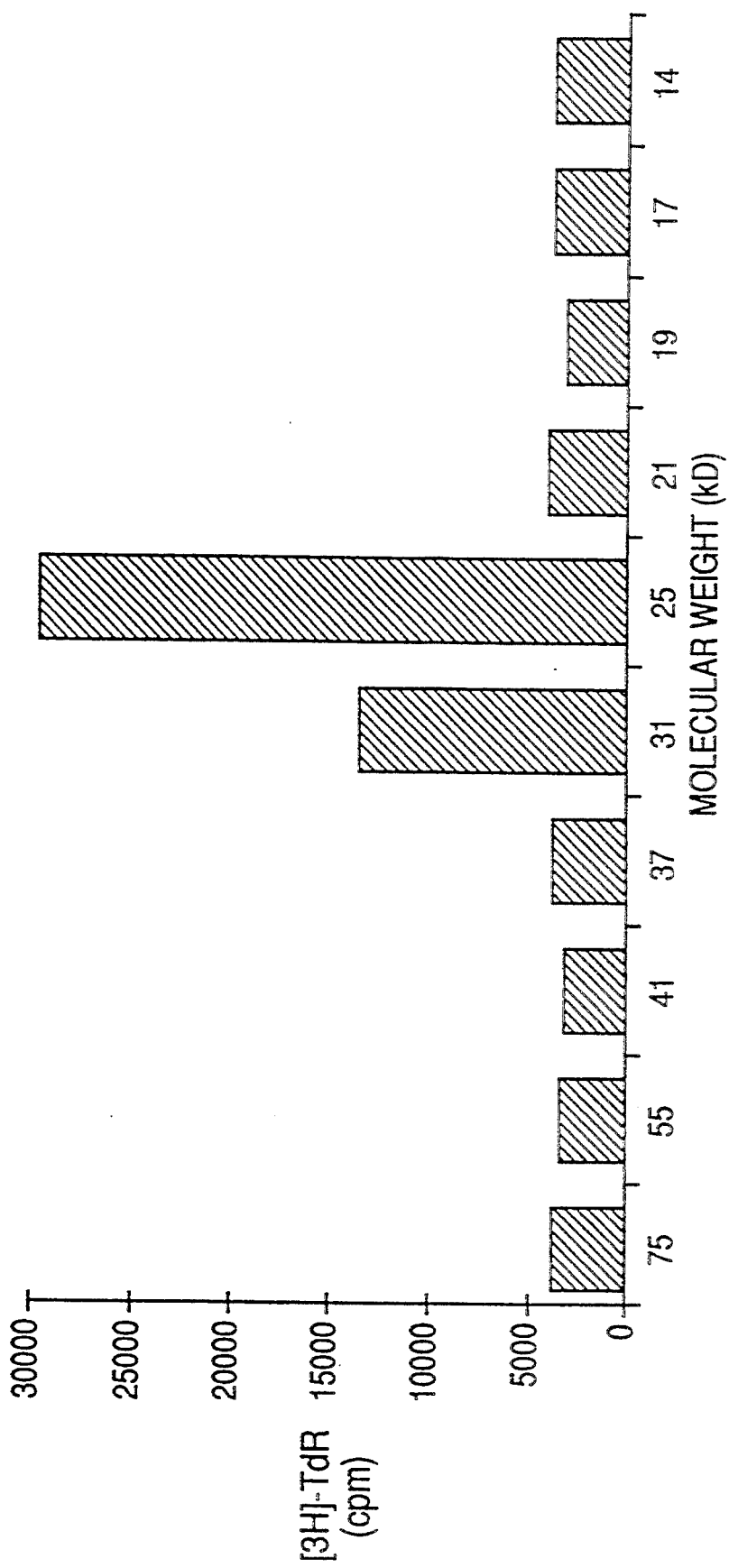
FIG. 11 shows the activity of materials eluted from an SDS-PAGE gel at the indicated molecular weights. Each eluate was tested for its ability to induce T cell proliferation in the presence of interleukin-2. The Y-axis represents tritiated thymidine incorporation by T cells exposed to the eluates.

The results indicate that the peak of SAF activity eluted with material of molecular weight 25 kD ±3 kD (FIG. 11). Material eluting at 14 kD had Little or no activity.

We claim:

1. A method of activating and stimulating replication of CD3+, CD4+ T cells comprising
treating CD3+, CD4+ T cells with a lymphokine preparation containing SAF activity in an amount effective to increase Tac expression and stimulate proliferation of said CD3+, CD4+ T cells.

2. The method of claim 1 wherein the CD3+, CD4+ T cells are in a preparation of peripheral blood mononuclear cells.

3. The method of claim 1 wherein the CD3+, CD4+ T cells are in a long-term T cell line and said T cell line is also treated with interleukin 2.

4. The method of claim 1 wherein the CD3+, CD4+ T cells are in the body of a human patient.

5. The method of claim 4 wherein the human patient is immunodeficient.

6. The method of claim 4 wherein the human patient displays Sezary Syndrome and the patient is also treated with cytotoxic chemotherapeutic agents to kill the Sezary T cells.

7. A method of activating and stimulating replication of CD3+, CD4+ T cells comprising:
treating a cell culture containing CD3+, CD4+ T cells with a lymphokine preparation containing SAF activity in an amount effective to increase Tac expression and stimulate proliferation of said CD3+, CD4+ T cells.

8. The method of claim 7 wherein said cell culture contains freshly isolated peripheral blood mononuclear cells.

9. The method of claim 8 wherein said freshly isolated peripheral blood mononuclear cells are from a Sezary Syndrome patient.

10. The method of claim 7 said cell culture contains a long term T cell line.

11. The method of claim 10 wherein said cell long term T cell line is a long term Sezary T cell line.

12. A method of activating and stimulating replication of CD3+, CD4+ T cells of a human patient comprising administering a lymphokine preparation containing SAF activity to a human patient in an amount effective to increase Tac expression and stimulate proliferation of CD3+, CD4+ T cells.

13. The method of claim 12 wherein the human patient is immunodeficient.

14. The method of claim 12 wherein the human patient displays Sezary Syndrome and the patient is also treated with cytotoxic chemotherapeutic agents to kill the Sezary T cells.

* * * * *